United States Patent [19]

Carmen

[11] Patent Number: 4,943,287
[45] Date of Patent: Jul. 24, 1990

[54] RED BLOOD CELL STORAGE SYSTEM

[75] Inventor: Raleigh A. Carmen, Concord, Calif.

[73] Assignee: Miles Inc., Elkhart, Ind.

[21] Appl. No.: 380,949

[22] Filed: Jul. 17, 1989

[51] Int. Cl.$^5$ .............................................. A61J 1/00
[52] U.S. Cl. ...................................... 604/408; 604/6; 210/206
[58] Field of Search .................. 604/406, 408, 410, 6, 604/262; 210/206

[56] References Cited

U.S. PATENT DOCUMENTS

| | | | |
|---|---|---|---|
| 4,140,162 | 2/1979 | Gajewski et al. | 604/408 X |
| 4,222,379 | 9/1980 | Smith | 604/410 |
| 4,280,479 | 7/1981 | Warner et al. | 604/408 |
| 4,301,800 | 11/1981 | Collins et al. | 604/408 X |
| 4,451,259 | 5/1984 | Geissler et al. | 604/408 |
| 4,505,708 | 3/1985 | Gajewski et al. | 604/408 |
| 4,559,053 | 12/1985 | Forges | 604/408 |
| 4,560,720 | 12/1985 | Aoyagi et al. | 604/408 X |
| 4,810,378 | 3/1989 | Carmen et al. | 604/410 X |

Primary Examiner—Mickey Yu
Assistant Examiner—Lynda M. Cofsky
Attorney, Agent, or Firm—James A. Giblin

[57] ABSTRACT

Closed blood bag system for long term storage of red blood cells (RBCs) without contamination due to storage. System comprises the combination of a white blood cell (WBC) filter in sterile communication with a plastic bag made from a film substantially free of blood extractable plasticizers. In use, an RBC preservative solution (preferably from within the closed system) is added to a mixture of RBCs and WBCs and the mixture is then passed through the filter to remove at least 98% of the WBCs. The filtered RBCs and preservative solution pass into the attached bag and can then be stored in the attached bag for up to 42 days.

10 Claims, 1 Drawing Sheet

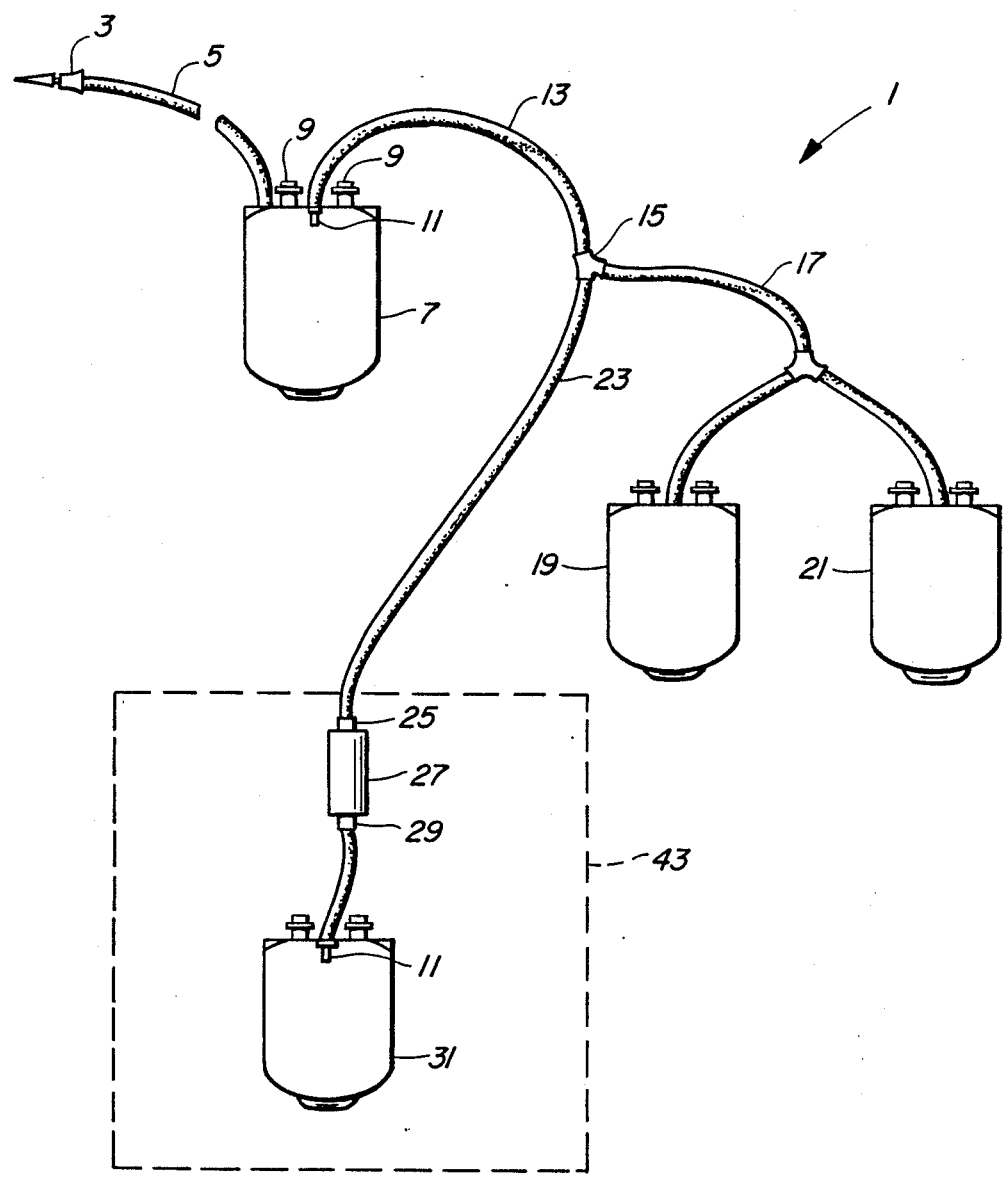

RED BLOOD CELL STORAGE SYSTEM

BACKGROUND OF THE INVENTION

1. Field

This disclosure is concerned generally with blood bag systems and specifically with a closed blood bag system useful for long term storage of red blood cells.

2. Prior art

The storage of red blood cells (RBCs) in containers, primarily plastic blood bags, is a well known and established practice. The RBCs are initially separated from whole blood in a container (plastic bag) by centrifugation of the whole blood. This results in a lower, denser RBC portion and an upper, lighter plasma portion. The upper plasma is then removed from the container by expressing it from an opening at the upper part of the container. The separated RBCs remaining in the container are then referred to as packed RBCs.

Packed RBCs can be stored for relatively long periods if a RBC preservation solution is then added. At present, using RBC storage solutions such as AS-1, AS-3, or SAGM, RBCs can be stored for up to 42 days and still be considered safe and useful. The bags used for long term storage of RBCs are typically made from a plastic film comprising polyvinyl chloride (PVC) plasticized with a plasticizer known as dioctylphthalate, also known as DOP. That plasticizer is also called diethylhexylphthalate, also known as DEHP, and that designation will be used in the remainder of this disclosure.

One criterion for the storability of RBCs is the amount of RBC hemolysis that occurs over time in a given RBC preservative solution. In U.S. Pat. No. 4,222,379 to D. Smith, DEHP plasticized PVC blood bags were said to be especially suitable for RBC storage after it was noted that relatively low amounts of hemolysis occurred when RBCs were stored in bags made from a film of that plastic. Although DEHP plasticized PVC blood bags had been available for many years, the above observation was made relatively recently and it led to several other disclosures based on related uses of that plasticizer system (e.g., the use of DEHP plasticized PVC inserts in a blood bag as in U.S. Pat. No. 4,301,800 to Collins and the use of DEHP in the form of an emulsion used in blood storage). See also, U.S. Pat. No. 4,451,259 to Geissler et al. disclosing the intentional use of DEHP in bags made from chlorine free polymers. Today, RBC storage systems capable of storing RBCs for the longest time (up to 42 days) continue to use blood bags made from DEHP plasticized PVC blood bags.

Unfortunately, DEHP is blood-extractable. This means that in time, especially with longer blood storage times of up to 42 days, the DEHP tends to leach into the stored blood or stored RBCs. Thus the observed benefit of using DEHP plasticized PVC containers to reduce hemolysis of RBCs stored for long periods is somewhat clouded because of concerns of DEHP contamination in a product intended for parenteral use in a human. See, for example, Blais P., DEHP IN BLOOD BAGS AND MEDICAL PLASTICS: THEIR LIMITATIONS. Canadian Research June/July 1981.

Although the exact cause of hemolysis in stored RBCs is not fully known, it is known that the expression of certain white blood cell (WBC) enzymes may contribute to RBC hemolysis, especially with time. See, for example, Hogman, CF et al., RED CELL PRESERVATION IN PROTEIN-POOR MEDIA 1. LEUKOCYTE ENZYMES AS A CAUSE OF HEMOLYSIS. Transfusion 1978, 18:233-241.

WBCs have been filtered from RBC/WBC mixtures to reduce the incidences of febrile reactions in patients receiving RBCs. See, for example, U.S. Pat. No. 4,810,378 to R. Carmen et. al. and U.S. Pat. No. 4,767,541 to L. Wisdom. However, such filtered RBCs are commonly passed into and stored in conventional DEHP plasticized PVC blood bags. This is not particularly surprising in view of the long time use and approval for blood storage of that plastic system. The relatively recent disclosures of the above-cited Smith, Collins and Geissler et al. patents provide added reasons for the continued use of that bag system for the long term storage of RBCs.

Non-DEHP/PVC plastic systems are being used for blood components other that RBCs (e.g., platelets can be stored in polyolefin bags or in bags made from a low extracting system of trioctyltrimellitate plasticized PVC as disclosed in U.S. Pat. No. 4,280,497 to Carmen et. al.). To date, however, those plastics have not been used for the long term storage of RBCs (storage of up to 42 days). Thus, to obtain the benefits of 42 day RBC storage, it has been common practice to use bags of DEHP plasticized PVC and simply accept the undesirable trade-off of continued DEHP contamination for low hemolysis (and 42 day storage).

Against the above background, we have attempted to see if the benefits of 42 day storage could be obtained without the disadvantages of DEHP contamination. Surprisingly, we have found that by combining the results of substantial WBC removal with the benefits of low blood extractable plastic films, it is now possible to obtain long term storage of RBCs without substantial contamination of the blood. Details of our findings are disclosed below.

SUMMARY OF THE INVENTION

Our closed system for the long term storage of RBCs comprises a white blood cell filter in sterile communication with a plastic bag made from plastic film substantially free of blood extractable plasticizers. The system is closed in the sense that once blood or RBCs enter the system, sterility is maintained during filtration and subsequent storage. See, for example, the description of closed blood bag systems in U.S. Pat. No. 4,586,928 to Barnes et al. The system is considered closed if the filter is initially pre-connected to the bag or if the filter is subsequently connected to the bag using so-called sterile docking techniques as disclosed, for example, in U.S. Pat. No. 4,507,119 to Spencer.

The non-extracting plastic may be made from a flexible film material of plasticized polyvinyl chloride which, on long term storage of contained RBCs, releases less than 1 ppm plasticizer into the stored RBC preparation (i.e. less than 1 mg per liter). A preferred PVC system comprises a bag made from a film of PVC plasticized with trioctyltrimellitate (TOTM), as disclosed in U.S. Pat. No. 4,289,497 to Warner et al. Alternatively, the film may be selected from non-plasticizer systems such as polyurethane, polyester, polycarbonate, polyolefins.

Our method of storing RBCs for prolonged and clinically acceptable periods (up to 42 days) comprises the steps of collecting packed red blood cells in a first blood bag, mixing the packed red blood cells with a red blood cell preservative solution, passing the mixture through a filter adapted to remove at least about 98% of the WBCs that are present in the mixture and then collecting and storing the RBCs for prolonged periods of time (up to 42 days) in a blood bag substantially free of blood extractable plasticizers. Substantially free of such plasticizer(s) means that less than 1 ppm of plasticizer is extracted into a unit (about 330 ml) of stored RBCs after 42 days under normal storage conditions. The bag is made from a non-extracting plasticized PVC system or a non-PVC plastic which does not use plasticizers, such as those described above. Key features of the system of this disclosure are the pre-storage removal of substantially WBCs ($\geq$98% of all WBCs originally present in the RBC/WBC mixture) and the subsequent storage of the filtered RBCs with an appropriate RBC preservative solution in a non-extracting plastic bag.

BRIEF DESCRIPTION OF THE FIGURE

The FIGURE shows a plan view of a preferred system showing a WBC filter pre-connected to a non-extracting plastic bag which preferably contains a RBC storage solution.

SPECIFIC DESCRIPTION

The invention of this disclosure is illustrated in the FIGURE, in which the key combination of components, a filter 27 capable of removing substantially all WBCs and a bag substantially free of blood extractable plasticizers, is shown within dotted box 43. In a preferred embodiment, the preservative solution is already in the closed system and contained in the bag prior to the filtration step. The system is used as follows: whole blood from a donor enters phlebotomy needle 3 and passes through conventional PVC tubing 5 into donor bag 7. A preferred donor bag 7 has conventional ports 9 and an internal frangible valve shown generally as 11.

After whole blood in donor bag 7 is centrifuged to form an upper less dense plasma portion and a lower packed RBC portion (with some WBC's), frangible valve 11 is opened and the upper plasma portion is expressed through PVC tubing 13 to the right of Y-connector 15 and further through tubing 17 into satellite bags 19 or 20 for further processing. Satellite bags 19 and 21 may be severed from the system at tubing 17 which is then sealed, leaving donor bag 7 connected to filter 27 and storage bag 31. Needle 3 is previously severed at tubing 5 which is also sealed.

The packed RBC's (with some normally present but undesired WBCs) are then reconstituted with the aqueous RBC preservative (or storage) solution by mixing. In a very preferred embodiment, the preservative solution is initially stored in final, non-extracting storage bag 31 until needed, thus assuring the maintenance of a closed system. When needed to reconstitute the packed RBCs in bag 7, frangible valve 11 of solution-containing bag 31 is opened and the preservative solution is passed through filter 21 (thereby also priming it) and into bag 7 via tubings 23 and 13. The packed RBCs and solution are mixed and the mixture is then expressed out of donor bag 7 through WBC filter 27 by passing the cells through entry port 25 and through exit port 29 of filter 27 into non-extracting bag 31 which also has conventional ports. In the preferred embodiment (preservative solution initially in bag 31), frangible valve (shown as 11) is now already opened to admit the filtered RBCs. In our preferred system, at least 98% of all WBCs initially in the packed RBC/WBC mixture are removed by filter 27. Since the preservative solution (e.g. AS-3) used to reconstitute the packed RBC/WBC mixture is already present in the filtered RBCs now in non-extracting bag 31, the bag 31 can now be severed from its connecting tubing and sealed for storage of the RBCs under conventional conditions for up to 42 days.

Our invention is illustrated in the following example and described use of a preferred bag system using a filter pre-connected to a TOTM plasticized PVC bag.

EXAMPLE

Construction of the preferred system

A TOTM plasticized PVC bag of the type described in U.S. Pat. No. 4,280,497 to Warner et al. was connected to a filter of the type described in U.S. Pat. No. 4,810,378 to Carmen et al.

Packed RBCs were introduced into the bag and a preservative solution known as AS-3 passed through the filter from the final non-extracting storage bag was mixed with the RBCs. The reconstituted RBCs were then passed through the filter by gravity and into the final non-extracting storage bag. The data below show that the RBCs could be stored for up to 42 days. At weekly intervals indicated below, various measurements were made to assess the effects of WBC removal (at least 98% of original WBCs were removed by the filter in each case) on the stored RBCs in a non DEHP/PVC storage bag. The results are shown in the Tables below.

TABLE I

STUDY 0809 - LEUKOPOOR AS-3 RBC STORED IN TOTM/ PVC BAG EXPERIMENTAL PROTOCOL - BBR P0172-080488
% HEMOLYSIS

| Donor # | Week 0 | Week 3 | Week 4 | Week 5 | Week 6 |
|---|---|---|---|---|---|
| 174 | 0.05 | 0.17 | 0.38 | 1.04 | 1.27 |
| 175 | 0.03 | 0.07 | 0.16 | 0.30 | 0.49 |
| 176 | 0.05 | 0.09 | 0.18 | 0.27 | 0.36 |
| 177 | 0.08 | 0.11 | 0.16 | 0.23 | 0.31 |
| 178 | 0.04 | 0.07 | 0.14 | 0.24 | 0.36 |
| 179 | 0.04 | 0.08 | 0.19 | 0.32 | 0.50 |
| Mean | 0.05 | 0.10 | 0.20 | 0.40 | 0.55 |
| S.D. | 0.02 | 0.04 | 0.09 | 0.32 | 0.36 |

TABLE II

ATP MICROMOLE/GRAM Hb

| Donor # | Week 0 | Week 3 | Week 4 | Week 5 | Week 6 |
|---|---|---|---|---|---|
| 174 | 4.46 | 3.32 | 3.23 | 2.48 | 2.15 |
| 175 | 4.65 | 4.38 | 4.39 | 3.21 | 3.05 |
| 176 | 4.91 | 3.72 | 3.31 | 2.55 | 2.40 |
| 177 | 5.12 | 5.15 | 4.79 | 3.84 | 3.23 |
| 178 | 4.77 | 3.70 | 3.36 | 2.51 | 2.04 |
| 179 | 5.41 | 4.49 | 4.68 | 3.57 | 3.37 |
| Mean | 4.89 | 4.13 | 3.96 | 3.03 | 2.71 |
| S.D. | 0.34 | 0.67 | 0.74 | 0.60 | 0.58 |

TABLE III

PLASMA POTASSIUM mEg/L

| Donor # | Week 0 | Week 3 | Week 4 | Week 5 | Week 6 |
|---|---|---|---|---|---|
| 174 | 3.60 | 28.70 | | | 42.40 |
| 175 | 3.90 | 29.20 | | | 41.80 |
| 176 | 3.20 | 28.40 | | | 43.00 |
| 177 | 3.50 | 25.60 | | | 38.80 |
| 178 | 4.20 | 32.50 | | | 47.40 |
| 179 | 3.20 | 26.90 | | | 40.70 |
| Mean | 3.60 | 28.55 | | | 42.35 |
| S.D. | 0.39 | 2.34 | | | 2.88 |

These data show that removing leukocytes prior to storage permits storage of red cells for up to 42 days in a non-DEHP/PVC container. Hemolysis was well below the 1% limit currently set by the FDA. Red cells from which leukocytes are not removed exhibit greater than 1% hemolysis when stored for extended periods in non-DEHP/PVC containers. ATP was well maintained, averaging 55.4% of initial value at 42 days, and potassium leakage was normal.

The system and method of this disclosure shows that, contrary to the teachings of the above-cited patents, long term (up to 42 days) storage of RBCs in a preservative solution is now possible without the use of plasticizers such as DEHP which are known to be blood extractable.

Given the above disclosure, it is thought that numerous variations will occur to those skilled in the art. Accordingly, it is intended that the above example should be considered only illustrative and that the scope of the invention disclosed herein should be limited only by the following claims.

We claim:

1. In a method of storing red blood cells which comprises mixing packed red blood cells and white blood cells with a storage solution and storing the mixture in a plastic blood bag for a prolonged period of time, the improvement which comprises removal of substantially all white blood cells from the mixture prior to placement of the mixture in the blood bag and then storing the red blood cells in a plasticized polyvinylchloride bag made with a plasticizer that releases less than 1 ppm plasticizer into the stored red blood cells at 42 days storage.

2. The method of claim 1 wherein at least 98% of the white blood cells ar removed prior to storage of the mixture.

3. The method of claim 2 wherein the white blood cells are removed by passing the mixture through a filter in sterile communication with the storage bag.

4. The method of claim 3 wherein the filter is adapted to be sterile docked to a second bag.

5. The method of claim 3 wherein the filter is in sterile communication with a second bag.

6. The method of claim 5 wherein the second bag is substantially free of blood extractable plasticizers.

7. The method of claim 6 wherein both the first and second bags are made from polyvinyl chloride plasticized with a plasticizer which, on long term contact with red blood cells, releases less than 1 ppm plasticizer into the stored red blood cells.

8. The method of claim 7 wherein one of the bags contains an aqueous solution.

9. The method of claim 8 wherein the aqueous solution is a red blood cell storage solution.

10. A method for storing red blood cells comprising the steps of
    (a) collecting packed red blood cells and white blood cells in a first blood bag;
    (b) mixing the packed red blood cells and white blood cells with a red blood cell preservative solution;
    (c) passing the mixture of step (b) through a filter adapted to remove at least 98% of the white blood cells that are present in the mixture; and
    (d) collecting and storing for prolonged periods of time the filtered mixture into a polyvinylchloride blood bag substantially free of blood extractable plasticizers which releases less than 1 ppm plasticizer into the stored red blood cells after 42 days storage under red blood cell storage conditions.

* * * * *